United States Patent
Vogl et al.

(10) Patent No.: US 10,687,711 B2
(45) Date of Patent: Jun. 23, 2020

(54) COMPUTERIZED DEVICE AND METHOD FOR PROCESSING IMAGE DATA

(71) Applicant: Medizinische Universität Wien, Vienna (AT)

(72) Inventors: Wolf-Dieter Vogl, Gänserndorf (AT); Thomas Schlegl, Vienna (AT); Georg Langs, Vienna (AT); Ursula Schmidt-Erfurth, Vienna (AT); Sebastian Waldstein, Vienna (AT); Bianca Gerendas, Vienna (AT)

( * ) Notice: Subject to any disclaimer, the term of this patent is extended or adjusted under 35 U.S.C. 154(b) by 0 days.

(21) Appl. No.: 15/571,480

(22) PCT Filed: May 3, 2016

(86) PCT No.: PCT/EP2016/059877
§ 371 (c)(1),
(2) Date: Nov. 2, 2017

(87) PCT Pub. No.: WO2016/177722
PCT Pub. Date: Nov. 10, 2016

(65) Prior Publication Data
US 2018/0132725 A1  May 17, 2018

(30) Foreign Application Priority Data
May 5, 2015 (EP) .................................... 15166379

(51) Int. Cl.
*A61B 5/00* (2006.01)
*G06K 9/62* (2006.01)
(Continued)

(52) U.S. Cl.
CPC .......... *A61B 5/0066* (2013.01); *A61B 3/0025* (2013.01); *A61B 3/102* (2013.01);
(Continued)

(58) Field of Classification Search
CPC .. A61B 3/10; A61B 3/00; A61B 3/102; A61B 3/0025; A61B 5/00; A61B 5/0066;
(Continued)

(56) References Cited

U.S. PATENT DOCUMENTS

| 8,879,813 | B1 | 11/2014 | Solanki et al. |
| 9,430,706 | B1 | 8/2016 | Peleg |

(Continued)

FOREIGN PATENT DOCUMENTS

| EP | 3065086 A1 | 9/2016 |
| WO | 2008133951 A2 | 11/2008 |

OTHER PUBLICATIONS

Cox, D.R. et al., "Analysis of Survival Data," CRC Press, vol. 21, Jun. 1, 1984, 18 pages.

(Continued)

*Primary Examiner* — Jie Lei
(74) *Attorney, Agent, or Firm* — Alleman Hall Creasman & Tuttle LLP (57) ABSTRACT

A computerized device for processing image data is proposed. The computerized device comprises a receiving unit a receiving unit which is configured to receive optical coherence tomography data of a tissue of a patient, in particular of a retina, a providing unit which is configured to provide a prediction model for processing the optical coherence tomography data, and a processing unit which is configured to process the received optical coherence tomography data using the prediction model for providing at least one prediction parameter for predicting prospective objects of the tissue and/or prospective features allocated to the tissue.

15 Claims, 5 Drawing Sheets

(51) Int. Cl.
| | |
|---|---|
| A61B 3/10 | (2006.01) |
| G06T 7/00 | (2017.01) |
| A61B 3/00 | (2006.01) |
| G06K 9/46 | (2006.01) |
| G06T 7/11 | (2017.01) |
| G06T 7/77 | (2017.01) |
| G06T 7/143 | (2017.01) |
| G06T 7/70 | (2017.01) |
| G06N 3/04 | (2006.01) |

(52) U.S. Cl.
CPC .......... *A61B 5/0073* (2013.01); *A61B 5/7267* (2013.01); *G06K 9/4623* (2013.01); *G06K 9/627* (2013.01); *G06T 7/0012* (2013.01); *G06T 7/11* (2017.01); *G06T 7/143* (2017.01); *G06T 7/70* (2017.01); *G06T 7/77* (2017.01); *G06K 2209/05* (2013.01); *G06N 3/0454* (2013.01); *G06T 2207/10101* (2013.01); *G06T 2207/20076* (2013.01); *G06T 2207/20081* (2013.01); *G06T 2207/20084* (2013.01); *G06T 2207/30041* (2013.01)

(58) Field of Classification Search
CPC ...... A61B 5/0073; A61B 5/7267; G06K 9/62; G06K 9/46; G06K 9/627; G06K 9/4623; G06K 2209/05; G06T 7/00; G06T 7/11; G06T 7/77; G06T 7/0012; G06T 7/143; G06T 7/70; G06T 2207/10101; G06T 2207/20076; G06T 2207/20081; G06T 2207/20084; G06T 2207/30041; G06N 3/0454
USPC .............. 351/206, 203, 207, 221, 205, 246; 600/425, 476
See application file for complete search history.

(56) References Cited

U.S. PATENT DOCUMENTS

| | | | |
|---|---|---|---|
| 9,779,492 | B1 | 10/2017 | Garnavi et al. |
| 9,824,189 | B2 | 11/2017 | Sawada et al. |
| 9,953,425 | B2 | 4/2018 | Lin et al. |
| 2005/0283450 | A1 | 12/2005 | Matsuga et al. |
| 2006/0204053 | A1 | 9/2006 | Mori et al. |
| 2010/0277691 | A1 | 11/2010 | Huang et al. |
| 2012/0184845 | A1 | 7/2012 | Ishikawa et al. |
| 2015/0201829 | A1 | 7/2015 | Yang et al. |
| 2016/0100806 | A1 | 4/2016 | Mwanza et al. |
| 2016/0117587 | A1 | 4/2016 | Yan et al. |

OTHER PUBLICATIONS

Zou, H. et al., "Regularization and variable selection via the elastic net," Statistical Methodology, vol. 67, Issue 2, Mar. 9, 2005, 20 pages.
Garvin, M. et al., "Automated 3-D Intraretinal Layer Segmentation of Macular Spectral-Domain Optical Coherence Tomography Images," IEEE Transactions on Medical Imaging, vol. 28, No. 9, Sep. 2009, 12 pages.
Myronenko, A. et al., "Point Set Registration: Coherent Point Drift," IEEE Transactions on Pattern Analysis and Machine Intelligence, vol. 32, Issue 12, Mar. 18, 2010, 14 pages.
Gonzalez, A. et al., "Automatic Cyst Detection in OCT Retinal Images Combining Region Flooding and Texture Analysis," IEEE 26th International Symposium on Computer-Based Medical Systems (CBMS), Jun. 20, 2013, Porto, Portugal, 4 pages.
Montuoro, A. et al., "Motion Artefact Correction in Retinal Optical Coherence Tomography using Local Symmetry," Medical Image Computing and Computer-Assisted Intervention—MICCAI 2014: 17th International Conference, Sep. 14, 2014, Boston, MA, USA, 8 pages.
Sadeghi, N. et al., "Subject-specific prediction using nonlinear population modeling: Application to early brain maturation from DTI," Medical Image Computing and Computer-Assisted Intervention—MICCAI 2014: 17th International Conference, Sep. 14, 2014, Boston, MA, USA, 8 pages.
Wu, J, et al., "Stable registration of pathological 3D-OCT scans using retinal vessels," Ophthalmic Medical Image Analysis First International Workshop, OMIA 2014, Held in Conjunction with MICCAI 2014, At MIT, Sep. 14, 2014, Boston, MA, USA, 10 pages.
Wu, J. et al., "Automated Retinal Fovea Type Distinction in Spectral-domain Optical Coherence Tomography of Retinal vein Occlusion," SPIE 9413, Medical Imaging 2015: Image Processing, Mar. 20, 2015, 8 pages.
ISA European Patent Office, International Search Report and Written Opinion Issued in PCT Application No. PCT/EP2016/059877, dated Jul. 27, 2016, WIPO, 13 pages.
Burgansky-Eliash, Z. et al., "Optical Coherence Tomography Machine Learning Classifiers for Glaucoma Detection: A Preliminary Study," In Journal of Investigative Opthalmology & Visual Science, vol. 46, No. 11, Nov. 2005, 6 pages.
Pradhan, S. et al., "Shallow Semantic Parsing using Support Vector Machines" In Proceedings of the Human Language Technology Conference (HLT/NAACL 2004), May 2, 2004, Boston, MA, USA, 9 pages.
Ciresan, D. et al., "Multi-column Deep Neural Networks for Image Classification", In Proceedings of the 2012 IEEE Conference on Computer Vision and Pattern Recognition (CVPR), Jun. 16, 2012, Providence, RI, USA, 8 pages.
Krizhevsky, A. et al., "ImageNet Classification with Deep Convolutional Neural Networks", In Proceedings of the Twenty-Sixth Annual Conference on Neural Information Processing Systems (NIPS), Dec. 3, 2012, Lake Tahoe, USA, 9 pages.
Zheng, Y. et al., "Computerized assessment of intraretinal and subretinal fluid regions in spectral-domain optical coherence tomography images of the retina," American Journal of Ophthalmology, 155.2, 2013, 11 pages.
Schlegl, T. et al., "Unsupervised Pre-training Across Image Domains Improves Lung Tissue Classification" Medical Computer Vision: Algorithims for Big Data, Dec. 10, 2014, 12 pages.
Schlegl, T. et al., "Automatic segmentation and classification of intraretinal cystoid fluid and subretinal fluid in 3d-oct using convolutional neural networks," Investigative Opthalmology & Visual Science, 56.7, 2015, 2 pages.
ISA European Patent Office, International Search Report and Written Opinion Issued in PCT Application No. PCT/EP2016/054249, dated May 23, 2016, WIPO, 15 pages.
Shah A., "Simultaneous Multiple Surface Segmentation Using Deep Learning," InDeep Learning in Medical Image Analysis and Multimodal Learning for Clinical Decision Support, Sep. 14, 2017, 8 pages.
United States Patent and Trademark Office, Office Action Issued in U.S. Appl. No. 15/554,414, dated Sep. 17, 2019, 26 pages.
K. McDonough et al.,"A neural network approach to retinal layer boundary identification from optical coherence tomography images,";2015 IEEE Conference on Computational Intelligence in Bioinformatics and Computational Biology (CIBCB), Niagara Falls, ON, 2015, 8 pages.
Yan, Z., et al., "HD-CNN: hierarchical deep convolutional neural network for image classification," In Proceedings of the IEEE international conference on computer vision, Dec. 7, 2015. 8 pages.
European Patent Office, Office Action Issued in Application No. 16720819.8, dated Oct. 9, 2019, Germany, 4 pages.
European Patent Office, Office Action Issued in Application No. 16706882.4, dated May 14, 2019, Netherlands, 5 pages.

COMPUTERIZED DEVICE AND METHOD FOR PROCESSING IMAGE DATA

FIELD OF THE INVENTION

The present invention relates to a computerized device and to a method for processing image data. The technical field of the present invention is the processing of image data, like medical image data. For example, said medical image data may be optical coherence tomography data provided by an optical coherence tomography scanner (OCT scanner).

BACKGROUND

In particular, a key driver for vision loss in retinal diseases such as neovascular age-related macular degeneration is the accumulation of retinal edema or fluid. Out of the two components of retinal edema, intraretinal cystoid fluid (IRC) leads to severe vision loss. Conversely, recent evidence suggests that subretinal fluid (SRF) may be associated with better visual acuity. A precise classification, quantification and prediction of IRC and SRF may be of great importance for disease management. Similarly, a wide spectrum of other quantifiable morphologic objects may be present in the retina, which may be relevant for visual function, diagnosis, disease management and prediction of visual function.

A conventional method for processing optical coherence tomography data for automatic cyst detection is described in reference [1]. But, the method described in reference [1] has disadvantages in the calculating speed and in the necessary accuracy.

Accordingly, it is an aspect of the present invention to improve the processing of image data, like optical coherence tomography data.

BRIEF SUMMARY OF THE INVENTION

According to a first aspect, a computerized device for processing image data is proposed. The computerized device comprises a receiving unit which is configured to receive optical coherence tomography data (OCT) of a tissue of a patient, a providing unit which is configured to provide a prediction model for processing the optical coherence tomography data (OCT), and a processing unit which is configured to process the received optical coherence tomography data (OCT) using the prediction model for providing at least one prediction parameter for predicting prospective objects of the tissue and/or prospective features allocated to the tissue. The patient may be a human or an animal. The tissue may be a human or animal tissue, for example a retina.

By processing the optical coherence tomography data by means of said prediction model, the present computerized device provides the beneficial technical effect of calculating said prospective (or future) objects of the tissue and/or said prospective (or future) features allocated to the tissue with a higher accuracy.

In particular, the optical coherence tomography data are provided by an optical coherence tomography scanner (OCT scanner) which is capable to scan the tissue, for example a retina of a human being or an animal.

The computerized device may be a computer or an embedded system, for example. The embedded system may be part of a scanner or may be coupled with that.

In an embodiment, the receiving unit is configured to receive a plurality of different optical coherence tomography data (OCT) of one patient at different times and/or a plurality of different optical coherence tomography data (OCT) of different patients.

Thus, the present computerized device may use intra-patient information and inter-patient information advantageously.

In a further embodiment, the providing unit is configured to normalize all the received optical coherence tomography data (OCT) by transforming all the received optical coherence tomography data (OCT) into a joint reference coordinate system.

In particular, the optical coherence tomography data (OCT) are in the form of longitudinal scans. To compensate anatomical and scanning position variations, the longitudinal scans are transformed into said joint reference coordinate system. Said joint reference coordinate system may be also denoted as joint reference space. In this joint reference space, spatio-temporal features are extracted from the OCT data describing the development of the underlying retinal structure and pathology, which may be finally used to predict clinical variables, such as objects and features. e.g. visual acuity and treatment response.

In a further embodiment, the object includes at least one of an intraretinal fluid, an intraretinal cystoid fluid (IRC), a subretinal fluid (SRF), a druse, a pseudodruse, a retinal layer, a choroidal layer, a pigment-epithelial detachment, a hyperreflective focus, a subretinal hyperreflective material, a hemorrhage, a vitreous membrane, an epiretinal membrane, and a retinal vessel.

In a further embodiment, the computerized device comprises a determining unit for determining objects in the tissue by processing the optical coherence tomography data (OCT) using a convolutional neural network (CNN).

E.g., the determining unit includes a further computerized device as described in the EP application 15157253.4. The content of said EP application 15157253.4 is incorporated by reference to the present patent application.

The further computerized device comprises a further providing unit which is configured to provide a convolutional neural network (CNN) for processing the optical coherence tomography data, and a further processing unit which is configured to process the received optical coherence tomography data using the convolutional neural network for identifying at least one certain object in the tissue The at least one certain object identified in the retina by processing said optical coherence tomography data using the convolutional neural network may include intraretinal cystoid fluids (IRC) and subretinal fluids (SRF).

The further processing unit is configured to process the received optical coherence tomography data using the convolutional neural network for outputting resulting image data. Said resulting image data may include the received optical coherence tomography data, wherein the at least one identified object is identified and/or marked in said optical coherence tomography data. For example, the resulting image data may include the optical coherence tomography data, intraretinal cystoid fluids (IRC) (in particular including their positions and volumes) and subretinal fluids (SRF) (in particular including their positions and locations).

By processing the optical coherence tomography data by means of said convolutional neural network, the further computerized device provides the beneficial technical effect of calculating said resulting image data faster and with a higher accuracy.

In particular, the convolutional neural network (CNN) is a hierarchically structured feed-forward neural network having one or more pairs of convolutional layers and succeeding max-pooling layers.

In further embodiment, the further processing unit is configured to localize the certain object in the optical coherence tomography data.

The locations of the certain objects in the optical coherence tomography data may be part of the resulting image data. For example, in the resulting image data, the certain objects are marked in the optical coherence tomography data, e.g., by a certain color.

In a further embodiment, the further processing unit is configured to quantify a volume of the certain object in the optical coherence tomography data.

The quantities of the certain objects in the optical coherence tomography data may be part of the resulting image data.

In a further embodiment, the further processing unit is configured to process the received optical coherence tomography data using the convolutional neural network for identifying intraretinal cystoid fluid and subretinal fluid in the received optical coherence tomography data.

In a further embodiment, the further processing unit is configured to segment and to classify the intraretinal cystoid fluid and the subretinal fluid in the received optical coherence tomography data.

In particular, the further processing unit is configured to automatically and highly accurately segment and discriminate between normal retinal tissue, intraretinal cystoid fluid and subretinal fluid in retinal optical coherence tomography data. This may enable precise structure-function correlations based on optical coherence tomography data on large scale. In this regard, the further processing unit uses said convolutional neural network to capture characteristic visual appearance patterns and classify normal retinal tissue, intraretinal cystoid fluid and subretinal fluid. In particular, the convolutional neural network may be trained by the providing unit in a supervised manner. In an experiment, the applicant trained the convolutional neural network using approximately 300,000 two-dimensional image patches extracted from 157 optical coherence tomography image volumes. In this experiment, all image patches were sampled at random positions. 73.43% of the patches show healthy tissue, 8.63% show IRC and 17.94% show SRF. Details for that are described in the EP application 15157253.4.

In a further embodiment, the further processing unit is configured to localize each of the intraretinal cystoid fluid regions and to localize each of the subretinal fluid regions in the optical coherence tomography data.

In particular, localization information for the locations of the intraretinal cystoid fluid and further localization information for the locations of the subretinal fluid may be incorporated to the resulting image data.

In a further embodiment, the further processing unit is configured to quantify a volume of each of the intraretinal cystoid fluid regions and to quantify a volume of each of the subretinal fluid regions in the optical coherence tomography data.

In particular, a quantity or volume of each of the intraretinal cystoid fluid regions and a further quantity or a further volume of each of the subretinal fluid regions may be incorporated into the resulting image data.

In a further embodiment, the optical coherence tomography data are spectral-domain optical coherence tomography images.

In a further embodiment, the providing unit is configured to train the prediction model on a design matrix having N rows and M columns, wherein each of the N rows is allocated to one of N patients and each of the M columns is allocated to one of M features, wherein each of the M features is allocated to at least one of the objects of the tissue.

In a further embodiment, the M features include at least one of a size of one of the objects, a volume of one of the objects, a location of one of the objects, a reflectivity of one of the objects, a texture of one of the objects, a polarization or retardation information of one of the objects, a distribution of the objects relative to each other, a visual acuity of one of the patients, a retinal sensitivity of one of the patients, a contrast sensitivity of one of the patients, a visual field of one of the patients, an age of one of the patients, a sex of one of the patients, and characteristics of treatments of one the patients.

In a further embodiment, the computerized device includes an obtaining unit for obtaining the features from the received optical coherence tomography data (OCT).

In a further embodiment, the features are spatio-temporal features.

In a further embodiment, the providing unit is configured to normalize the features of the received optical coherence tomography data (OCT) by transforming them into the same joint reference coordinate system as the normalized optical coherence tomography data (OCT).

In a further embodiment, the providing unit is configured to train the prediction model on the design matrix using the normalized optical coherence tomography data (OCT) and the normalized features.

In a further embodiment, the at least one prediction parameter includes at least one of a visual function at the same time point or in the future, one of the objects in the future, one of the features in the future, a recurrence of a certain disease, a recurrence interval of the disease, an appearance of a future OCT image, a derived feature of the future OCT image, a development of a visual function over time, a treatment response, a time to a next recurrence, a time to a next required treatment, a likelihood of success of a single treatment, and a time to a next required follow-up examination. Treatments may include for example antiangiogenic substances (ranibizumab, aflibercept, bevacizumab), steroids (triamcinolone, dexamethasone implants) or vitreolytic agents (ocriplasmin).

In a further embodiment, the prediction model is a multivariate sparse generalized linear model, in particular a sparse logistic regression for binary decision outcomes, a sparse multinomial regression for nominal outcomes, an elastic net regularized linear regression for continuous outcomes or sparse Cox regression for survival outcomes, a random forest model or a mixed effects regression model. Aspects of the mixed effects regression model are described in reference [9].

In a further embodiment, the receiving unit is configured to receive the optical coherence tomography data (OCT) of the tissue and clinical data related to the patient, and wherein the processing unit is configured to process the received optical coherence tomography data (OCT) using the received clinical data and the prediction model for providing the at least one prediction parameter for predicting the prospective objects of the tissue, the prospective features allocated to the tissue and/or prospective clinical data related to the patient.

In a further embodiment, the clinical data related to the patient includes at least one of a treatment of the patient, a time of treatment of the patient, a treatment response of the patient, a visual acuity of the patient, a retinal sensitivity of the patient, a contrast sensitivity of the patient, a visual field of the patient, an age of the patient, and a sex of the patient.

The respective unit, e.g. the providing unit or the processing unit, may be implemented in hardware and/or in software. If said unit is implemented in hardware, it may be embodied as a device, e.g. as a computer or as a processor or as a part of a system, e.g. a computer system. If said unit is implemented in software it may be embodied as a computer program product, as a function, as a routine, as a program code or as an executable object.

Any embodiment of the first aspect may be combined with any embodiment of the first aspect to obtain another embodiment of the first aspect.

According to a second aspect, a method for processing image data is proposed. The method includes a step of receiving optical coherence tomography data (OCT) of a tissue of a patient, a step of providing a prediction model for processing the optical coherence tomography data (OCT), and a step of processing the received optical coherence tomography data (OCT) using the prediction model for providing at least one prediction parameter for predicting prospective objects of the tissue and/or prospective features allocated to the tissue.

In particular, the present computerized device and the present method are adapted to predict future clinical parameters, objects or features of the retina based on a series of OCT images and clinical parameters. Outcome variables may be for instance the occurrence of certain objects such as retinal cysts observed in future OCT images, or whether the retina of a patient will exhibit recurring edema in diseases such as Retinal Vein Occlusion (RVO), or that time-point at which the recurrence will occur.

An embodiment of the present method may include the following steps a) to c):

a) Each OCT image is transferred into a joint (or common) reference coordinate system via image registration (normalization) to compensate for the variation in scanning positions within follow-up scans, scanning resolutions, and to compensate for the variation in retinal anatomy between patients.

b) Spatio-temporal features describing the underlying disease, such as total retinal thickness, change in total retinal thickness over time, interretinal cyst (IRC) and subretinal fluid (SRF) are extracted. These features are transformed in the joint reference coordinate system.

c) Based on the spatio-temporal features and outcome variables from a training dataset a sparse or non-linear regression model is trained, which can be applied on a new series of OCT images to predict the outcome variable for that subject.

In the following, the steps a) to c) are described in more detail:

a) Joint Reference Coordinate System:

The retinal OCT images are normalized by transforming the data into a joint reference coordinate system by first aligning the intra-patient follow-up scans based on the vessel structure visible in OCT images, followed by an inter-patient alignment via landmarks visible in OCT and fundus images.

First, motion artifacts are reduced in OCT images introduced by patient movement during acquisition by the method described in reference [2]. To obtain landmarks for the intra-patient follow-up registration automatic vessel segmentation is performed on the OCT images. Parameters for the affine registration are generated by applying Coherent Point Drift (see reference [3]) to the segmented retinal vessel point sets, as described in reference [4].

The inter-patient affine registration is performed by aligning the fovea center and the optic disc center position, where the fovea center is the origin of the new coordinate system, and the optic disc center position defines the rotation and scaling. The optic disc position is set in the joint coordinate system to 5.6 degree from the horizontal axis, and the distance optic disc to fovea center to 4.3 mm, which are population means [Rohrschneider 2004, Lujan et al. 2008]. The foveal center landmark (center of the fovea pit) is determined automatically using a method described in reference [5]. Since in macular centered OCT images the optic disk is not visible, the corresponding fundus or SLO image acquired at the same time is used. The disc is detected by applying a circular Hough transformation with varying radii and picking the radius with the highest response. The center of the circle is defined as the center of the optic disc. Right eyes are mirrored, in order to align their anatomy with scans from the left eye.

After these steps all scans within a subject and in between subjects are normalized to a joint reference coordinate system centered at fovea.

b) Spatio-Temporal Features in the Joint Reference Coordinate System:

Spatio-temporal features are extracted from the follow-up OCT images, transformed into the reference coordinate system (or space) and pooled into a vector per subject. Such features can be for instance the total retinal thickness map, which is the distance between the inner limiting membrane (ILM) surface, and the retinal pigment epithelium (RPE). These layers are identified using a graph-based surface segmentation algorithm (see reference [6]). Other features are change of thickness over time as the difference of two subsequent thickness maps, IRC and SRF maps for several layers in the retina, where each pixel in the map represents the height of the IRC or SRF. These maps are transformed into the joint coordinate system by applying the corresponding affine transformation of the OCT onto the map.

Additional features such as summary statistics (total cyst volume, area etc.) as well as clinical variables like age, sex, number of treatments may be added to the feature vector.

These feature maps for each acquisition timepoint and the additional features are concatenated into a feature vector with the size M. Finally, these feature vectors for each of the N subjects are pooled into a design matrix $X \in R^{N \times M}$, where each row represents a feature vector of a subject, and each column is either a distinct spatio-temporal anatomical position in the retina, if the feature is based on a map like the thickness map, or summary features like cyst volume, or clinical variables.

c) Prediction of Recurrence:

The prediction of the outcome variables is proposed as a multi-variate sparse generalized linear model (GLM), where the outcome variable (or function) is assumed to be a weighted linear combination of the input feature vector x: $y = w_0 + w_1 x_1 + w_2 x_2 + \ldots w_M x_M = wx$. The coefficients w are estimated from the design-matrix X and the corresponding outcome variables y by minimizing following objective function:

$$\operatorname*{argmin}_w \frac{1}{2N} * \|y - Xw\|_2^2 + \lambda * 11_{ratio} * \|w\|_1 + \lambda/2 * (1 - 11_{ratio}) * \|w\|_2^2$$

where the weights w are forced to be sparse by regularizing them via elastic net (see reference [7]). With this method continuous variables can be predicted, as for instance visual acuity or future total retinal thickness. By replacing the outcome variable y with a function, also other types of variables can be predicted, as for instance binary, multinomial or survival variables. For binary and multinomial variables the logit function is used, also known as logistic regression. Survival variables can be predicted by using the Cox proportional hazard model (see reference [8]). Binary variables may be for instance if a patient will suffer from a recurring edema within a follow-up period, and survival outcomes may describe the (relative) risk of having an edema at a specific timepoint. The objective function of the elastic net regularized logistic regression is:

$$\operatorname*{argmin}_{w} \sum_{i}^{N} \log(1 + \exp(-y_i w^T x_i)) +$$

$$\lambda * 11_{ratio} * \|w\|_1 + \lambda/2 * (1 - 11_{ratio}) * \|w\|_2^2$$

Respectively the coefficients for the Cox proportional hazard model are obtained by minimizing the regularized negative partial log-likelihood:

$$\operatorname*{argmin}_{w} - \sum_{r \in D} \left( x_r w - \log\left( \sum_{j \in R_i} \exp(x_j w) \right) \right) +$$

$$\lambda * 11_{ratio} * \|w\|_1 + \lambda/2 * (1 - 11_{ratio}) * \|w\|_2^2$$

where D is the set of indices of patient events and $R_i$ is the set of indices of individuals which are at risk at timepoint $t_i$.

According to a third aspect, the invention relates to a computer program comprising a program code for executing the method of the second aspect for processing image data when run on at least one computer.

In the following, exemplary embodiments of the present invention are described with reference to the enclosed figures.

BRIEF DESCRIPTION OF THE DRAWINGS

Similar or functionally similar elements in the figures have been allocated the same reference signs if not otherwise indicated.

DETAILED DESCRIPTION OF THE EMBODIMENTS

Figure 1:
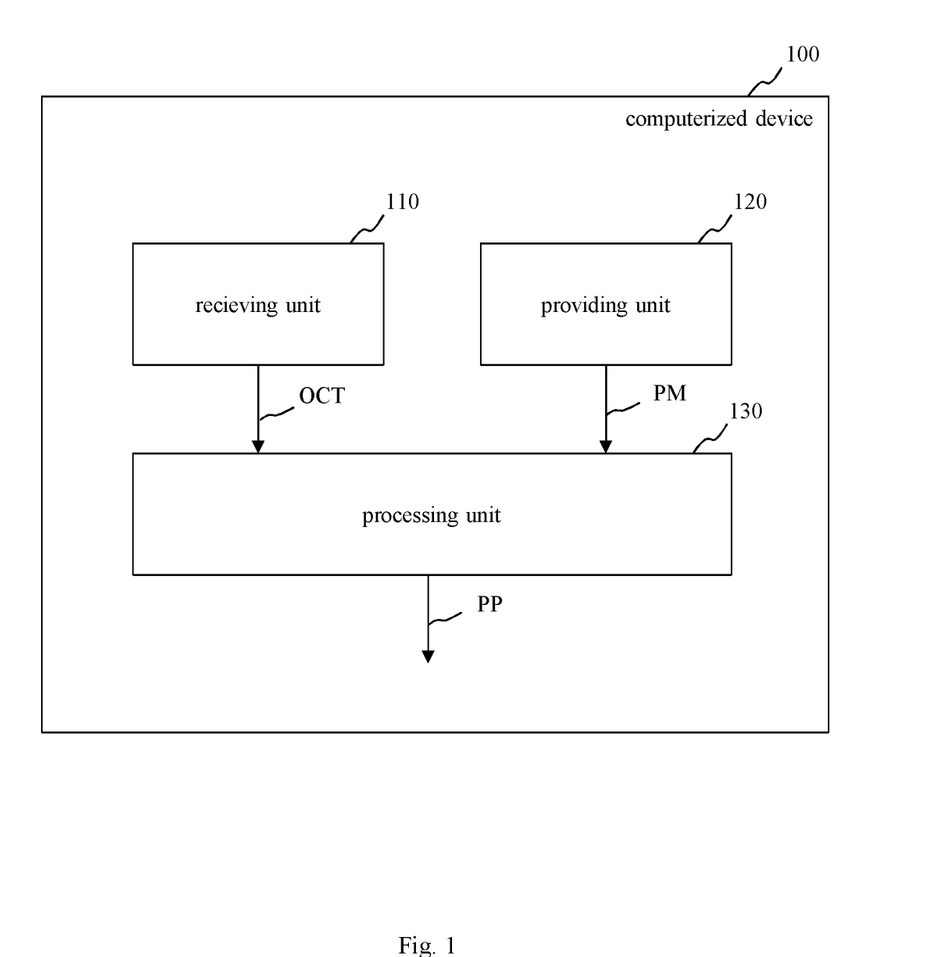
FIG. 1 shows a schematic block diagram of a first embodiment of a computerized device for processing image data.

In FIG. 1, a schematic block diagram of a first embodiment of a computerized device 100 for processing image data, in particular optical coherence tomography data OCT of a tissue, e.g. of a retina or of a skin, is depicted. Moreover, FIG. 2 shows a schematic block diagram of a system including the computerized device 100 of FIG. 1, an OCT scanner 200 for providing the optical coherence tomography data OCT and a display 300 for displaying a result, for example prediction parameters calculated by the computerized device 100.

Figure 2:
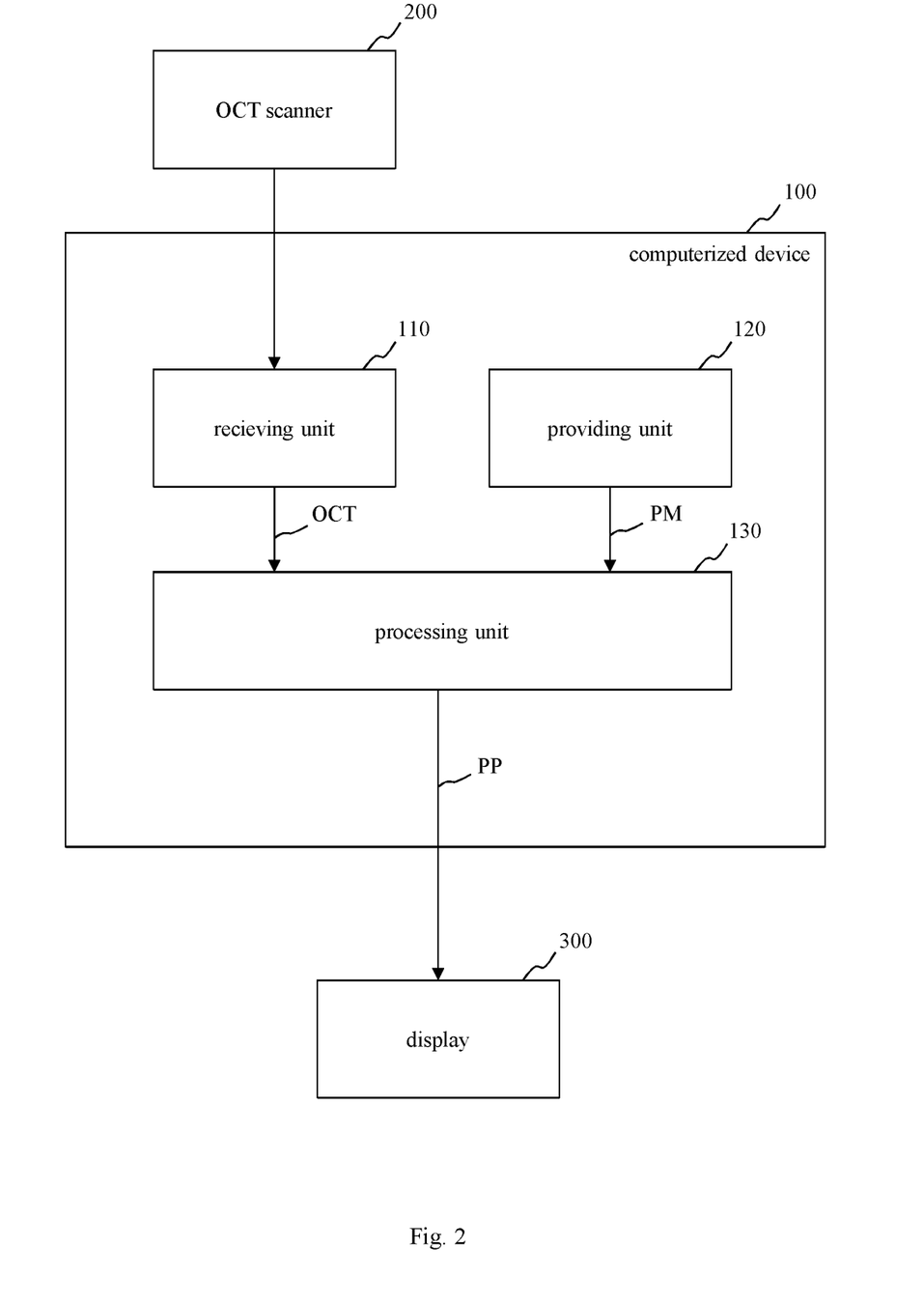
FIG. 2 shows a schematic block diagram of a system including the computerized device of FIG. 1, an optical coherence tomography scanner and a display.

The computerized device 100 of FIG. 1 and FIG. 2 includes a receiving unit 110, a providing unit 120 and a processing unit 130. For example, the computerized device 100 of FIG. 1 is embodied as a computer or as an embedded system.

The receiving unit 110 is configured to receive optical coherence tomography data OCT of a tissue of a patient, in particular of a retina. The patient may be a human or an animal.

For example, the optical coherence tomography data OCT are spectral-domain optical coherence tomography images.

The providing unit 120 is configured to provide a prediction model PM for processing the optical coherence tomography data (OCT). For example, the prediction model PM is a multivariate sparse generalized linear model, in particular a sparse logistic regression for binary decision outcomes, a sparse multinomial regression for nominal outcomes, an elastic net regularized linear regression for continuous outcomes or sparse Cox regression for survival outcomes. Alternatively, the prediction model PM may be a random forest model.

The processing unit 130 is configured to process the received optical coherence tomography data OCT using the prediction model PM for providing at least one prediction parameter PP for predicting prospective objects O of the tissue and/or prospective features F allocated to the tissue.

The objects O may include at least one of an intraretinal fluid, intraretinal cystoid fluid (IRC), a subretinal fluid (SRF), a druse, a pseudodruse, a retinal layer, a choroidal layer, a pigment-epithelial detachment, a hyperreflective focus, a subretinal hyperreflective material, a hemorrhage, a vitreous membrane, an epiretinal membrane, and a retinal vessel.

The features F may include at least one of a size of one of the objects, a volume of one of the objects O, a location of one of the objects O, a reflectivity of one of the objects O, a texture of one of the objects O, a polarization or retardation information of one of the objects O, a distribution of the objects O relative to each other, a visual acuity of one of the patients, a retinal sensitivity of one of the patients, a contrast sensitivity of one of the patients, a visual field of one of the patients, an age of one of the patients, a sex of one of the patients, and characteristics of previous treatments of one the patients.

The at least one prediction parameter PP may include at least one of a visual function at the same time point or in the future, one of the objects O in the future, one of the features F in the future, a recurrence of a certain disease, a recurrence interval of the disease, an appearance of a future OCT image, a derived feature of the future OCT image, a development of a visual function over time, a treatment response, a time to a next recurrence, a time to a next required treatment, a likelihood of success of a single treatment, and a time to a next required follow-up examination.

In particular, the receiving unit 110 may be configured to receive a plurality of different optical coherence tomography data OCT of one patient at different times and a plurality of different optical coherence tomography data OCT of different patients. Moreover, the providing unit 120 may be configured to normalize all the received optical coherence tomography data OCT by transforming all said received optical coherence tomography data OCT into a joint reference coordinate system.

The providing unit 120 may be configured to train the protection model PM on a design matrix having N rows and M columns, wherein each of the N rows allocated to one of N patients and each of the M columns is allocated to one of M features.

Figure 3:
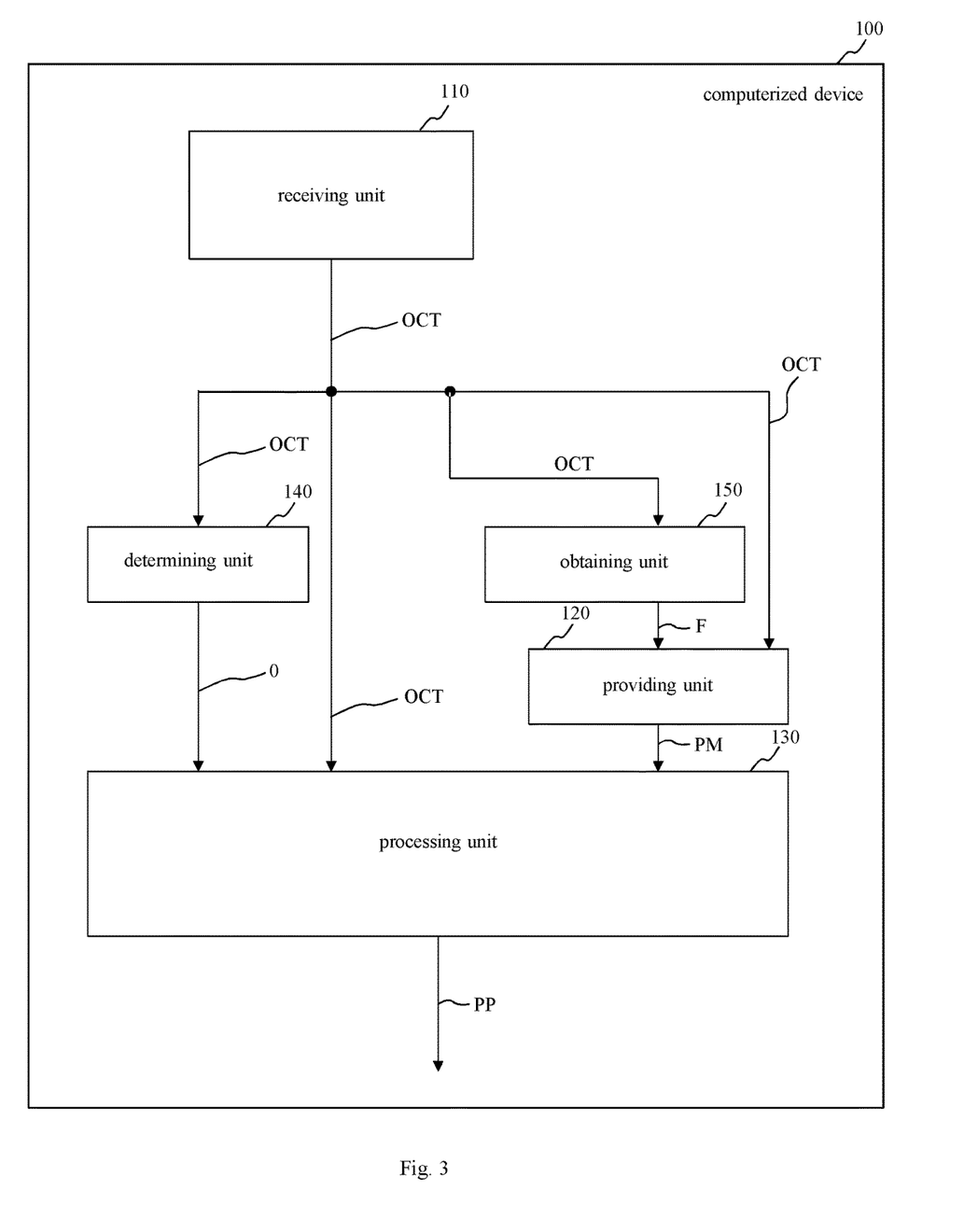
FIG. 3 shows a schematic block diagram of a second embodiment of a computerized device for processing image data.

In FIG. 3, a schematic block diagram of a second embodiment of a computerized device 100 for processing image data, in particular optical coherence tomography data OCT of a tissue, is shown.

The second embodiment of the computerized device 100 of FIG. 3 includes all features of the first embodiment of FIG. 1. Additionally, the second embodiment of the computerized device 100 of FIG. 3 has a determining unit 140 and an obtaining unit 150. The determining unit 140 is configured to determine objects O in the tissue by processing the optical coherence tomography data OCT using a convolutional neural network (CNN).

Moreover, the obtaining unit 150 is configured to obtain the features F from the received optical coherence tomography data OCT. In this regard, the providing unit 120 may be configured to normalize the features F of the received optical coherence tomography data OCT by transforming them into the same joint reference coordinate system as the normalized optical coherence tomography data OCT.

Furthermore, the providing unit 120 may be configured to train the prediction model PM on the design matrix using the normalized optical coherence tomography data OCT and the normalized features F. The design matrix may have N rows and M columns. Each of the N rows may be allocated to one of N patients and each of the M columns may be allocated to one of M features F, wherein each of the M features is allocated to at least one of the objects O of the tissue.

Figure 4:
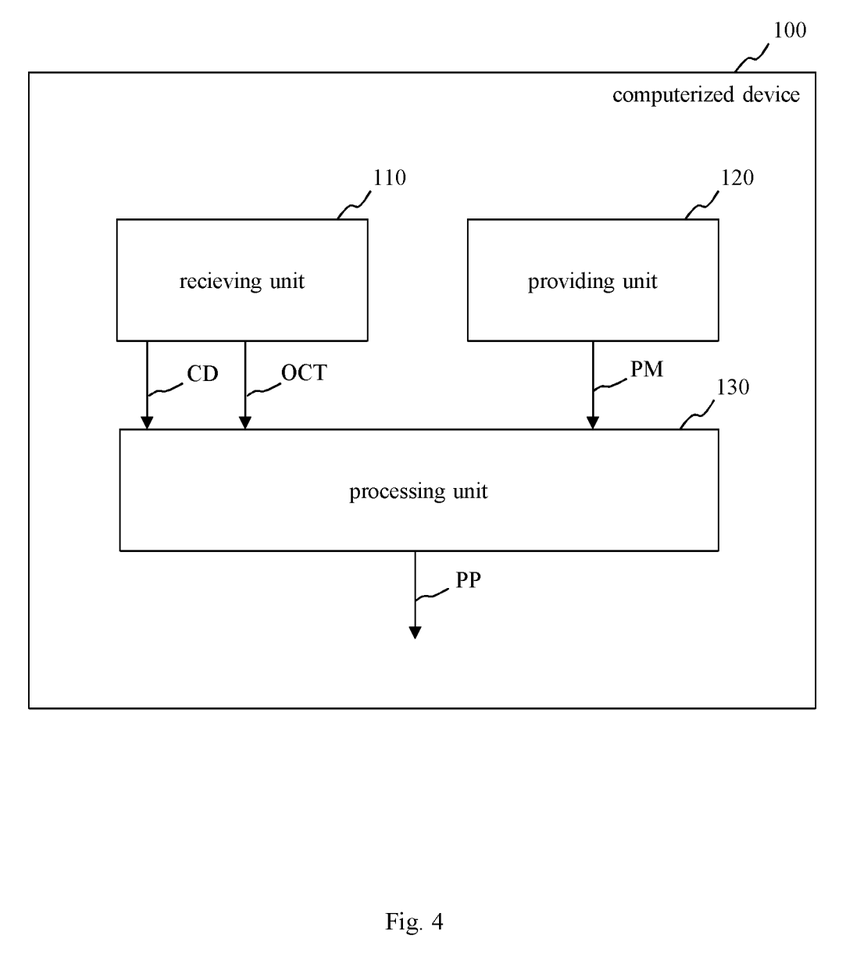
FIG. 4 shows a schematic block diagram of a third embodiment of a computerized device for processing image data.

FIG. 4 shows a schematic block diagram of a third embodiment of a computerized device 100 for processing image data. The third embodiment of the computerized device 100 of FIG. 4 includes all features of the first embodiment of FIG. 1. Additionally, the receiving unit 110 of FIG. 4 is configured to receive not only the optical coherence tomography data OCT of the tissue, but also clinical data CD that are related to the patient.

The clinical data CD related to the patient may include at least one of a treatment of the patient, a time of treatment of the patient, a treatment response of the patient, a visual acuity of the patient, a retinal sensitivity of the patient, a contrast sensitivity of the patient, a visual field of the patient, an age of the patient, and a sex of the patient.

In this regard, the processing unit 130 of FIG. 4 is configured to process the received optical coherence tomography data OCT using the received clinical data CD and the prediction model PM for providing the at least one prediction parameter PP for predicting the prospective objects O of the tissue, the prospective features F allocated to the tissue and prospective clinical data CD related to the patient.

Figure 5:
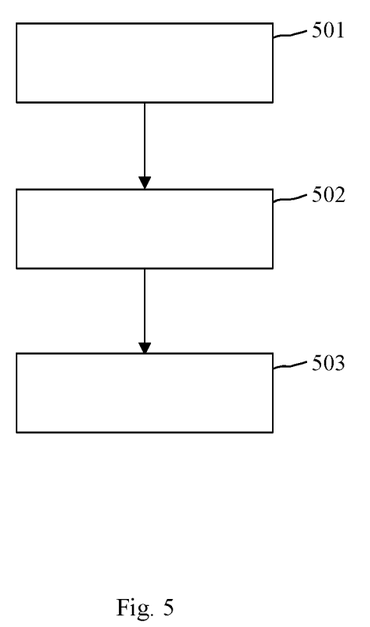
FIG. 5 shows an embodiment of a sequence of method steps for processing image data.

In FIG. 5, a sequence of method steps for processing image data OCT is depicted. The method of FIG. 5 includes the following method steps 501-503:

In step 501, optical coherence tomography data OCT of a tissue of a patient, in particular of a human or animal tissue, for example of a retina or of a skin, are received.

In step 502, a prediction model PM for processing the optical coherence tomography data OCT is provided.

In step 503, the received optical coherence tomography data OCT are processed by using the provided prediction model PM for providing at least one prediction parameter PP for predicting prospective objects O of the tissue and/or prospective features F allocated to the tissue.

Computerized devices may be suitably designed for implementing embodiments of the present invention as described herein. Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages.

In particular, each block of the block diagrams may be implemented by one or more computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

More generally, while the present invention has been described with reference to certain embodiments, it will be understood by those skilled in the art that various changes may be made and equivalents may be substituted without departing from the scope of the present invention. In addition, many modifications may be made to adapt a particular situation to the teachings of the present invention without departing from its scope. Therefore, it is intended that the present invention not be limited to the particular embodiments disclosed, but that the present invention will include all embodiments falling within the scope of the appended claims.

REFERENCE. NUMERALS

100 computerized device
110 receiving unit
120 providing unit
130 processing unit
140 determining unit
150 obtaining unit
200 computer tomography scanner
300 display
501 method step
502 method step
503 method step
CD clinical data
F features
O objects
OCT optical coherence tomography data
PM prediction model
PP prediction parameter

REFERENCES

[1] González, A., Remeseiro, B., Ortega, M., Penedo, M. G., & Charlon, P.: Automatic cyst detection in OCT retinal images combining region flooding and texture analysis. In Computer-Based Medical Systems (2013) 397-400

[2] Montuoro, A., Wu, J., Waldstein, S., Gerendas, B., Langs, G., Simader, C., Schmidt-Erfurth, U.: Motion artifact correction in retinal optical coherence tomography using local symmetry. In Golland, P., Hata, N., Barillot, C., Hornegger, J., Howe, R., eds.: Medical Image Computing and Computer-Assisted Intervention—MICCAI 2014. Volume 8674 of Lecture Notes in Computer Science. Springer International Publishing (2014) 130-137

[3] Myronenko, A., Song, X.: Point set registration: Coherent point drift. IEEE Transactions on Pattern Analysis and Machine Intelligence 32(12) (2010) 2262-2275

[4] Wu, J., Gerendas, B. S., Waldstein, S. M., Langs, G., Simader, C., Schmidt-Erfurth, U.: Stable registration of pathological 3d-oct scans using retinal vessels. In Chen, X., Garvin, M. K., Liu, J. J., eds.: Proceedings of the Ophthalmic Medical Image Analysis First International Workshop, OMIA 2014, Held in Conjunction with MICCAI 2014, Iowa Research Online (2014) 1-8

[5] Wu, J., Gerendas, B. S., Waldstein, S. M., Langs, G., Simader, C.; Schmidt-Erfurth U.: Automated retinal fovea type distinction in spectral-domain optical coherence tomography of retinal vein occlusion. Proc. SPIE 9413, Medical Imaging 2015: Image Processing (2015);

[6] Garvin, M. K., Abramoff, M. D., Wu, X., Russell, S. R., Burns, T. L., Sonka, M.: Automated 3-d intraretinal layer segmentation of macular spectral-domain optical coherence tomography images. IEEE Transactions on Medical Imaging 28(9) (2009) 1436-1447

[7] Zola, H., Hastie, T.: Regularization and variable selection via the elastic net. Journal of the Royal Statistical Society: Series B (Statistical Methodology) 67(2) (2005) 301-320

[8] Cox, D. R., Oakes, D.: Analysis of survival data. Volume 21. CRC Press (1984)

[9] Sadeghi, N., Fletcher, P. T., Prastawa, M., Gilmore, J. H., Gerig, G.: Subject Specific Prediction Using Nonlinear Population Modeling: Application to Early Brain Maturation from DTI. In: Medical Image Computing and Computer-Assisted Intervention—MICCAI 2014: 17th International Conference, Boston, Mass., USA, Sep. 14-18, 2014, Proceedings, Part III. Springer International Publishing, Cham (2014) 33-40

The invention claimed is:

1. A computerized device for processing image data, the computerized device comprising:
a receiving unit which is configured to receive optical coherence tomography data of a tissue of a patient, in particular of a retina,
a providing unit which is configured to provide a prediction model for processing the optical coherence tomography data, and
a processing unit which is configured to process the received optical coherence tomography data using the prediction model for providing at least one prediction parameter for predicting future prospective objects of the tissue and/or future prospective features allocated to the tissue,
wherein the receiving unit receives a plurality of different optical coherence tomography data of one patient at different times and a plurality of different optical coherence tomography data of different patients,
wherein the providing unit carries out a normalization of the retinal optical coherence tomography images by transforming the data into a joint reference coordinate system by first aligning the intra-patient follow-up scans based on the vessel structure visible in optical coherence tomography images, followed by an inter-patient alignment using the fovea center and the optic disc center position, where the fovea center is the origin of the new coordinate system, and the optic disc center position defines a rotation and scaling, and
wherein the processing unit directly extracts from the optical coherence tomography data spatio-temporal features, without intervening steps of extracting summary parameters and/or parameter combination/reduction.

2. The computerized device of claim 1,
wherein the providing unit is configured to normalize all the received optical coherence tomography data by transforming all the received optical coherence tomography data into a joint reference coordinate system.

3. The computerized device of claim 1,
wherein the objects include at least one of an intraretinal fluid, intraretinal cystoid fluid, a subretinal fluid, a druse, a pseudodruse, a retinal layer, a choroidal layer, a pigment-epithelial detachment, a hyperreflective focus, a subretinal hyperreflective material, a hemorrhage, a vitreous membrane, an epiretinal membrane, and a retinal vessel.

4. The computerized device of claim 3, further comprising:
a determining unit for determining objects in the tissue by processing the optical coherence tomography data using a convolutional neural network.

5. The computerized device of claim 1,
wherein the providing unit is configured to train the prediction model on a design matrix having N rows and M columns, wherein each of the N rows is allocated to one of N patients and each of the M columns is allocated to one of M features, wherein each of the M features is allocated to at least one of the objects of the tissue.

6. The computerized device of claim 5,
wherein the M features include at least one of a size of one of the objects, a volume of one of the objects, a location of one of the objects, a reflectivity of one of the objects, a texture of one of the objects, a polarization or retardation information of one of the objects, a distribution of the objects relative to each other, a visual acuity of one of the patients, a retinal sensitivity of one of the patients, a contrast sensitivity of one of the patients, a visual field of one of the patients, an age of one of the patients, a sex of one of the patients, and characteristics of previous treatments of one the patients.

7. The computerized device of claim 6, further comprising:
an obtaining unit for obtaining the features from the received optical coherence tomography data.

8. The computerized device of claim 7,
wherein the providing unit is configured to normalize the features of the received optical coherence tomography data by transforming them into a same joint reference coordinate system of the normalized optical coherence tomography data.

9. The computerized device of claim 8,
wherein the providing unit is configured to train the prediction model on the design matrix using the normalized optical coherence tomography data and the normalized features.

10. The computerized device of claim 1,
wherein the at least one prediction parameter includes at least one of a visual function at the same time point or in the future, one of the objects in the future, one of the features in the future, a recurrence of a certain disease, a recurrence interval of the disease, an appearance of a future optical coherence tomography image, a derived feature of the future optical coherence tomography image, a development of a visual function over time, a treatment response, a time to a next recurrence, a time to a next required treatment, a likelihood of success of a single treatment, and a time to a next required follow-up examination.

11. The computerized device of claim 1,
wherein the prediction model is a multivariate sparse generalized linear model, in particular a sparse logistic regression for binary decision outcomes, a sparse multinomial regression for nominal outcomes, an elastic net regularized linear regression for continuous outcomes or sparse Cox regression for survival outcomes, a random forest model or a mixed effects regression model.

12. The computerized device of claim 1,
wherein the receiving unit is configured to receive the optical coherence tomography data of the tissue and clinical data related to the patient, and
wherein the processing unit is configured to process the received optical coherence tomography data using the received clinical data and the prediction model for providing the at least one prediction parameter for predicting the future prospective objects of the tissue, the future prospective features allocated to the tissue, and/or prospective clinical data related to the patient.

13. The computerized device of claim 12,
wherein the clinical data related to the patient includes at least one of a treatment of the patient, a time of treatment of the patient, a treatment response of the patient, a visual acuity of the patient, a retinal sensitivity of the patient, a contrast sensitivity of the patient, a visual field of the patient, an age of the patient, and a sex of the patient.

14. The computerized device of claim 1,
wherein the objects include at least one of an intraretinal fluid, an intraretinal cystoid fluid, and a subretinal fluid, a druse, a pseudodruse, a retinal layer, a choroidal layer, a pigment-epithelial detachment, a hyper-reflective focus, a subretinal hyperreflective material, a hemorrhage, a vitreous membrane, an epiretinal membrane, and a retinal vessel, and
the prediction parameter includes at least one of visual function at the same time point or in the future, a development of a visual function over time, a treatment response, a time to a next required treatment, a likelihood of success of a single treatment, and a time to a next required follow-up examination.

15. A method for processing image data, the method comprising:
receiving, by a receiving unit, optical coherence tomography data of a tissue of a patient, in particular of a retina, providing, by a providing unit, a prediction model for processing the optical coherence tomography data, and processing, by a processing unit, the received optical coherence tomography data using the prediction model for providing at least one prediction parameter for predicting future prospective objects of the tissue and/or future prospective features allocated to the tissue, wherein the receiving unit receives a plurality of different optical coherence tomography data of one patient at different times and a plurality of different optical coherence tomography data of different patients, wherein the providing unit carries out a normalization of the retinal optical coherence tomography images by transforming the data into a joint reference coordinate system by first aligning the intra-patient follow-up scans based on the vessel structure visible in optical coherence tomography images, followed by an inter-patient alignment using the fovea center and the optic disc center position, where the fovea center is the origin of the new coordinate system, and the optic disc center position defines a rotation and scaling, and wherein the processing unit directly extracts from the optical coherence tomography data spatio-temporal features, without intervening steps of extracting summary parameters and/or parameter combination/reduction.

* * * * *